US012582813B2

(12) United States Patent
Zaniboni

(10) Patent No.: US 12,582,813 B2
(45) Date of Patent: Mar. 24, 2026

(54) BLOOD CONDITIONING ASSEMBLY FOR USE WITH AN EXTRACORPOREAL LIFE SUPPORT SYSTEM

(71) Applicant: Sorin Group Italia S.r.l., Milan (IT)

(72) Inventor: Andrea Zaniboni, San Martino Spino (IT)

(73) Assignee: Sorin Group Italia S.r.l., Milan (IT)

( * ) Notice: Subject to any disclaimer, the term of this patent is extended or adjusted under 35 U.S.C. 154(b) by 996 days.

(21) Appl. No.: 17/691,777

(22) Filed: Mar. 10, 2022

(65) Prior Publication Data

US 2023/0285737 A1    Sep. 14, 2023

(51) Int. Cl.
| | |
|---|---|
| *A61M 60/113* | (2021.01) |
| *A61M 1/16* | (2006.01) |
| *A61M 60/237* | (2021.01) |
| *A61M 60/38* | (2021.01) |
| *A61M 60/422* | (2021.01) |
| *A61M 60/82* | (2021.01) |

(52) U.S. Cl.
CPC ........ *A61M 60/113* (2021.01); *A61M 1/1698* (2013.01); *A61M 60/237* (2021.01); *A61M 60/38* (2021.01); *A61M 60/422* (2021.01); *A61M 60/82* (2021.01)

(58) Field of Classification Search
CPC .. A61M 60/113; A61M 60/237; A61M 60/38; A61M 60/422; A61M 60/82; A61M 1/1698
See application file for complete search history.

(56) References Cited

U.S. PATENT DOCUMENTS

| | | | |
|---|---|---|---|
| 5,205,721 A | 4/1993 | Isaacson | |
| 5,270,005 A | 12/1993 | Raible | |
| 5,634,892 A | 6/1997 | Whalen | |
| 5,692,882 A | 12/1997 | Bozeman, Jr. et al. | |
| 6,117,390 A * | 9/2000 | Corey, Jr. ........... | A61M 60/825 |
| | | | 422/44 |
| 6,135,729 A | 10/2000 | Aber | |
| 6,244,835 B1 | 6/2001 | Antaki et al. | |
| 6,264,635 B1 | 7/2001 | Wampler et al. | |
| 6,976,996 B1 | 12/2005 | Aboul-Hosn | |

(Continued)

FOREIGN PATENT DOCUMENTS

| | | | | |
|---|---|---|---|---|
| DE | 29907332 U1 * | 9/1999 | ......... | A61M 1/1015 |
| EP | 1810704 A2 | 7/2007 | | |

(Continued)

OTHER PUBLICATIONS

International Search Report and Written Opinion for International Application No. PCT/IB2020/052855 dated Dec. 8, 2020.

*Primary Examiner* — Ariana Zimbouski
(74) *Attorney, Agent, or Firm* — Seager, Tufte & Wickhem LLP

(57) ABSTRACT

A blood conditioning assembly for use with an extracorporeal life support system may include an oxygenator including a housing and a gas exchanger disposed within the housing, and an axial pump extending from the housing and configured to drive fluid flow through the oxygenator. The axial pump may be integrally formed with the housing of the oxygenator. The blood conditioning assembly may be devoid of external tubing between the axial pump and the oxygenator.

14 Claims, 4 Drawing Sheets

(56)     References Cited

U.S. PATENT DOCUMENTS

| | | | |
|---|---|---|---|
| 7,374,574 B2 * | 5/2008 | Nuesser | F04D 13/0646 |
| | | | 623/3.15 |
| 7,762,941 B2 | 7/2010 | Jarvik | |
| 7,896,832 B2 | 3/2011 | Zafirelis et al. | |
| 8,088,059 B2 | 1/2012 | Jarvik | |
| 8,366,381 B2 * | 2/2013 | Woodard | A61M 60/508 |
| | | | 415/104 |
| 9,345,826 B2 | 5/2016 | Kenley et al. | |
| 2009/0032469 A1 | 2/2009 | Panzani et al. | |
| 2009/0180924 A1 | 7/2009 | Niitsuma | |
| 2012/0277653 A1 | 11/2012 | Olsen et al. | |
| 2016/0095969 A1 * | 4/2016 | Maurer | A61M 1/262 |
| | | | 264/263 |
| 2018/0001012 A1 | 1/2018 | Ardehali | |
| 2021/0338997 A1 | 11/2021 | Cecer et al. | |
| 2021/0393941 A1 | 12/2021 | Hansen | |

FOREIGN PATENT DOCUMENTS

| | | | |
|---|---|---|---|
| EP | 3574939 A1 | 12/2019 | |
| WO | 2019166823 A1 | 9/2019 | |
| WO | 2021191661 A1 | 9/2021 | |

* cited by examiner

BLOOD CONDITIONING ASSEMBLY FOR USE WITH AN EXTRACORPOREAL LIFE SUPPORT SYSTEM

TECHNICAL FIELD

The present disclosure relates generally to extracorporeal circulation. More particularly, the present disclosure relates to extracorporeal blood conditioning devices and methods for conditioning blood in extracorporeal circulation.

BACKGROUND

Generally, hollow fiber blood oxygenators that are used to exchange oxygen (O2) and carbon dioxide (CO2) in extracorporeal circulation during cardiac surgery have one of two forms. Either the oxygenator has a cylindrical housing with a crisscross hollow fiber mat spirally wound around a cylindrical central core, or the oxygenator has a polygonal housing with stacked (piled) hollow fiber mat layers. Blood flows outside the hollow fiber lumens and oxygenating gases flow inside the hollow fiber lumens.

In cylindrically wound oxygenators, blood flow across the hollow fibers may be radial, longitudinal, circumferential, or a combination of two or more of these. Often, this leads to a blood flow path that is relatively long and non-laminar to guarantee high gas exchange efficiency with reduced surface area and limited device priming volume, which are important parameters for optimal patient perfusion. If the blood path is too long, the resulting pre-oxygenator to post-oxygenator pressure gradient may be elevated, causing excessive mechanical stress and possible damage to blood cells. Also, at times, the pressure gradient may become so high that it is not possible to reach a desired extracorporeal blood flow rate, especially if the heart lung machine (HLM) pump, used to force blood through the extracorporeal circuit, is of the centrifugal (nonocclusive) type.

In some Extracorporeal Life Support (ECLS) systems, the oxygenator and pump are separate components. The patient undergoing ECLS treatment is normally cannulated via femoral or neck veins/artery. As a result, long tubing lines, needed to circulate patient blood in a closed loop, are used to connect the patient to all of the components of the ECLS, which are typically placed on a trolley. In some ECLS systems, the centrifugal pump may be integrated into the oxygenator, but must still be connected to an external driving unit, again requiring long tubing lines. The long tubing lines and/or the trolley may limit patient mobility and/or ambulation. As it is important to remove or prevent the formation of gas bubbles in an extracorporeal circuit, long tubing lines can make de-bubbling of the circuit at start-up of the ECLS a more complex and time-consuming process than with shorter tubing lines. One additional drawback of the long tubing lines may include high priming blood volume (the volume of blood outside of the patient), which may be compensated for using saline solution that leads to significant hemodilution and hematocrit reduction.

There is an ongoing need for alternative ECLS devices, components, and/or methods of use and/or manufacture of said devices and/or components.

SUMMARY

In one example, a blood conditioning assembly for use with an extracorporeal life support system may comprise an oxygenator including a housing and a gas exchanger disposed within the housing, and an axial pump extending from the housing and configured to drive fluid flow through the oxygenator. The axial pump may be integrally formed with the housing of the oxygenator.

In addition or alternatively to any example disclosed herein, the housing includes a blood outlet port configured to connect to the extracorporeal life support system.

In addition or alternatively to any example disclosed herein, the blood outlet port is disposed on an opposite side of the gas exchanger from the axial pump.

In addition or alternatively to any example disclosed herein, the axial pump includes an inlet having an inlet flow axis and an outlet having an outlet flow axis, wherein the inlet flow axis is coaxial with the outlet flow axis.

In addition or alternatively to any example disclosed herein, the axial pump includes a helical impeller having a central axis that is coaxial with the inlet flow axis and the outlet flow axis.

In addition or alternatively to any example disclosed herein, the helical impeller is magnetically suspended within a pump body of the axial pump.

In addition or alternatively to any example disclosed herein, the axial pump includes a rectifier disposed downstream of the helical impeller.

In addition or alternatively to any example disclosed herein, the rectifier is stationary with respect to the pump body.

In addition or alternatively to any example disclosed herein, the rectifier includes a cylindrical body and a helical ridge extending along an outer surface of the cylindrical body.

In addition or alternatively to any example disclosed herein, a blood conditioning assembly for use with an extracorporeal life support system may comprise an oxygenator including a housing and a gas exchanger disposed within the housing, and an axial pump configured to drive fluid flow through the oxygenator. The blood conditioning assembly may be devoid of external tubing between the axial pump and the oxygenator.

In addition or alternatively to any example disclosed herein, the axial pump is disposed coaxial with an inflow lumen of the oxygenator.

In addition or alternatively to any example disclosed herein, the axial pump includes an inlet having an inlet flow axis and the housing includes a blood outlet port having a blood outlet flow axis, wherein the inlet flow axis is generally parallel to the blood outlet flow axis.

In addition or alternatively to any example disclosed herein, the axial pump includes a helical impeller having one or more magnets embedded therein.

In addition or alternatively to any example disclosed herein, the one or more magnets embedded in the helical impeller interact with a rotating magnetic field generated by one or more stator windings disposed within a pump body of the axial pump.

In addition or alternatively to any example disclosed herein, an extracorporeal life support system may comprise a blood conditioning assembly including an oxygenator including a housing and a gas exchanger disposed within the housing. The blood conditioning assembly may include an axial pump configured to drive fluid flow through the oxygenator. The axial pump may be fixedly attached directly to the oxygenator. The extracorporeal life support system may comprise an arterial flow tube fluidly connected to an artery of a patient and coupled to a blood outlet port of the housing. The extracorporeal life support system may comprise a venous flow tube fluidly connected to a vein of the patient and coupled to an inlet of the axial pump.

In addition or alternatively to any example disclosed herein, the housing includes a venous cover and an arterial cover disposed on opposite sides of the gas exchanger.

In addition or alternatively to any example disclosed herein, the axial pump includes a pump body disposed tangentially on the venous cover.

In addition or alternatively to any example disclosed herein, the axial pump includes a pump body integrally formed with the housing.

In addition or alternatively to any example disclosed herein, the axial pump includes a helical impeller disposed within a pump body, the helical impeller being rotatable relative to the pump body.

In addition or alternatively to any example disclosed herein, one or more magnets prevent physical contact between the helical impeller and the pump body.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
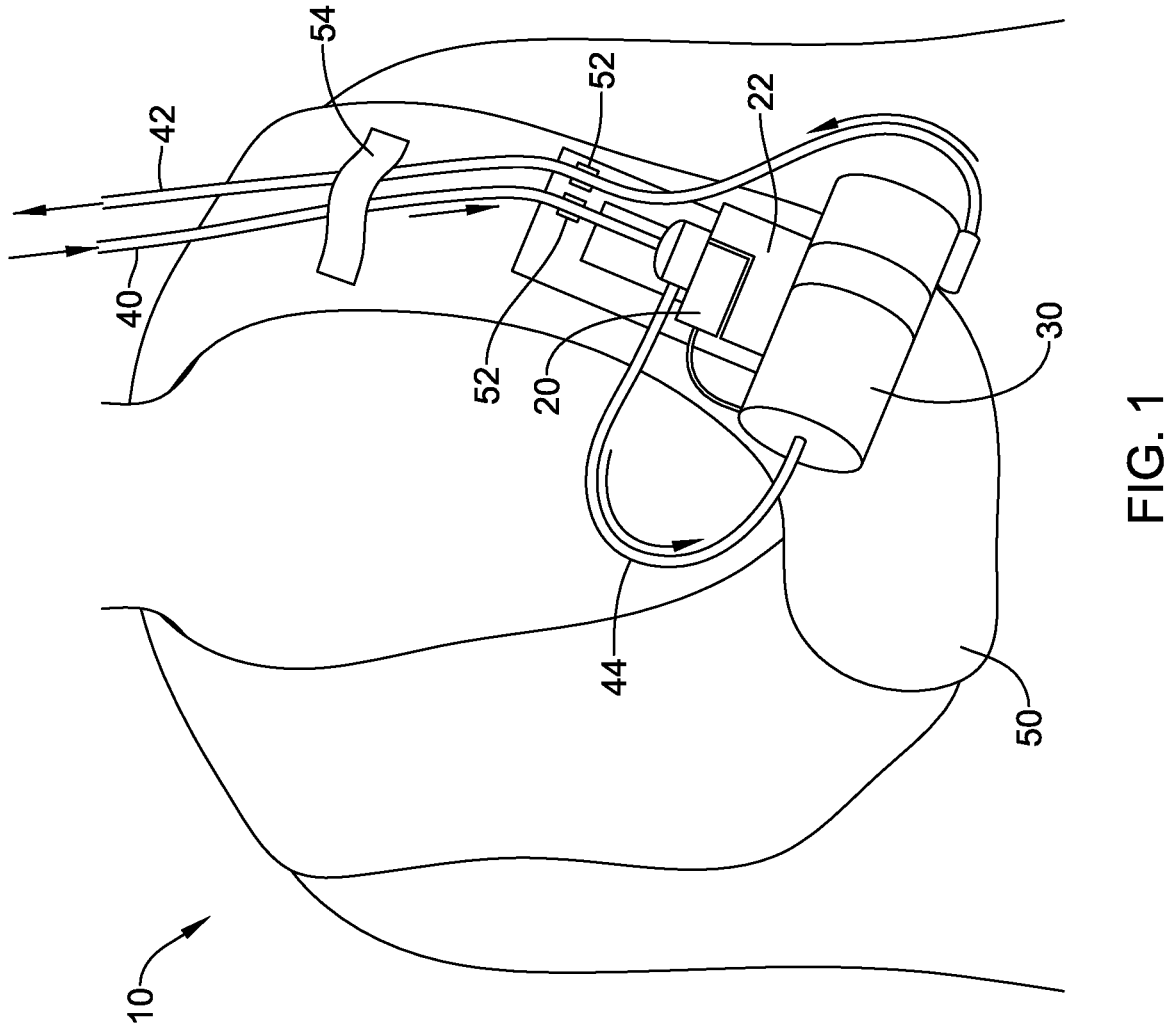
FIG. 1 illustrates selected aspects of an ECLS system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate example embodiments of the disclosure but not limit the disclosure. Those skilled in the art will recognize that the various elements described and/or shown may be arranged in various combinations and configurations without departing from the scope of the disclosure. However, in the interest of clarity and ease of understanding, every feature and/or element may not be shown in each drawing.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about"

may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered the greatest possible dimension measured according to the intended usage, while a "minimum extent" may be considered the smallest possible dimension measured according to the intended usage. In some instances, an "extent" may generally be measured orthogonally within a plane and/or cross-section, but may be, as will be apparent from the particular context, measured differently-such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to some features may be equally referred to all instances and quantities beyond one of said feature(s) unless clearly stated to the contrary. As such, it will be understood that the following discussion may apply equally to any and/or all of the components for which there are more than one within the device, etc. unless explicitly stated to the contrary.

Additionally, it should be noted that in any given figure, some features may not be shown, or may be shown schematically, for clarity and/or simplicity. Additional details regarding some components and/or method steps may be illustrated in other figures in greater detail. The devices and/or methods disclosed herein may provide a number of desirable features and benefits as described in more detail below.

FIG. 1 illustrates selected aspects of an extracorporeal life support (ECLS) system 10. The ECLS system 10 may include a motor integrated with a centrifugal pump to form a pump assembly 20, and a separate oxygenator 30. The ECLS system 10 may include tubing forming a blood inflow line 40, a blood outflow line 42, and a blood transfer line 44. The blood inflow line 40 may fluidly connect the patient's vein to the pump assembly 20. The blood outflow line 42 may fluidly connect the oxygenator 30 to the patient's artery. The blood transfer line 44 may fluidly connect the pump assembly 20 to the oxygenator 30 for transfer of blood from the pump assembly 20 to the oxygenator 30. In at least some embodiments, the blood inflow line 40, the blood outflow line 42, and/or the blood transfer line 44 may be formed from 0.375-inch polymeric tubing. Other tubing sizes are also possible. In some instances, the ECLS system 10 may include and/or may be coupled to and/or integrated into a wearable support garment 50 (e.g., a strap or belt, a vest such as the VoyagerVest® from CardiacAssist, Inc., etc.), thereby rendering the ECLS system 10 more portable than conventional systems utilizing a trolley. The pump assembly 20 may be coupled to and/or received by a mount 22. The mount 22 may be secured to the oxygenator 30 and/or the wearable support garment 50. The oxygenator 30 may be secured to the wearable support garment 50. The wearable support garment 50 may include clips 52 and/or straps 54 to secure the tubing (e.g., the blood inflow line 40, the blood outflow line 42, etc.) to the wearable support garment 50.

The total volume of fluid contained in the ECLS system 10 defines a volume of extracorporeal blood and/or fluid. The current disclosure describes an ECLS system having features that may reduce the volume of extracorporcal blood and/or fluid in, and/or may improve the efficiency of, the ECLS system.

Figure 2:
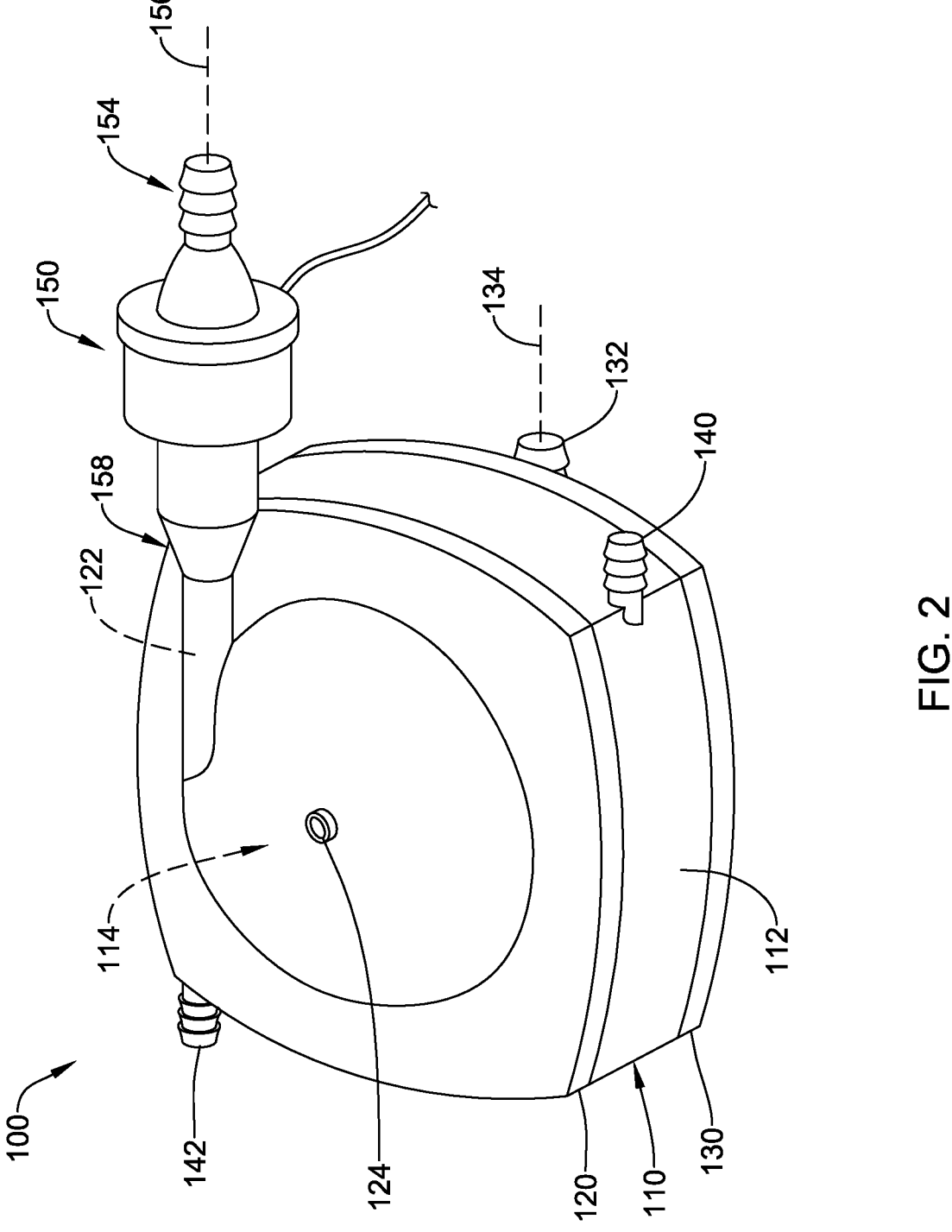
FIG. 2 illustrates selected aspects of a blood conditioning assembly according to the disclosure.
Figure 3:
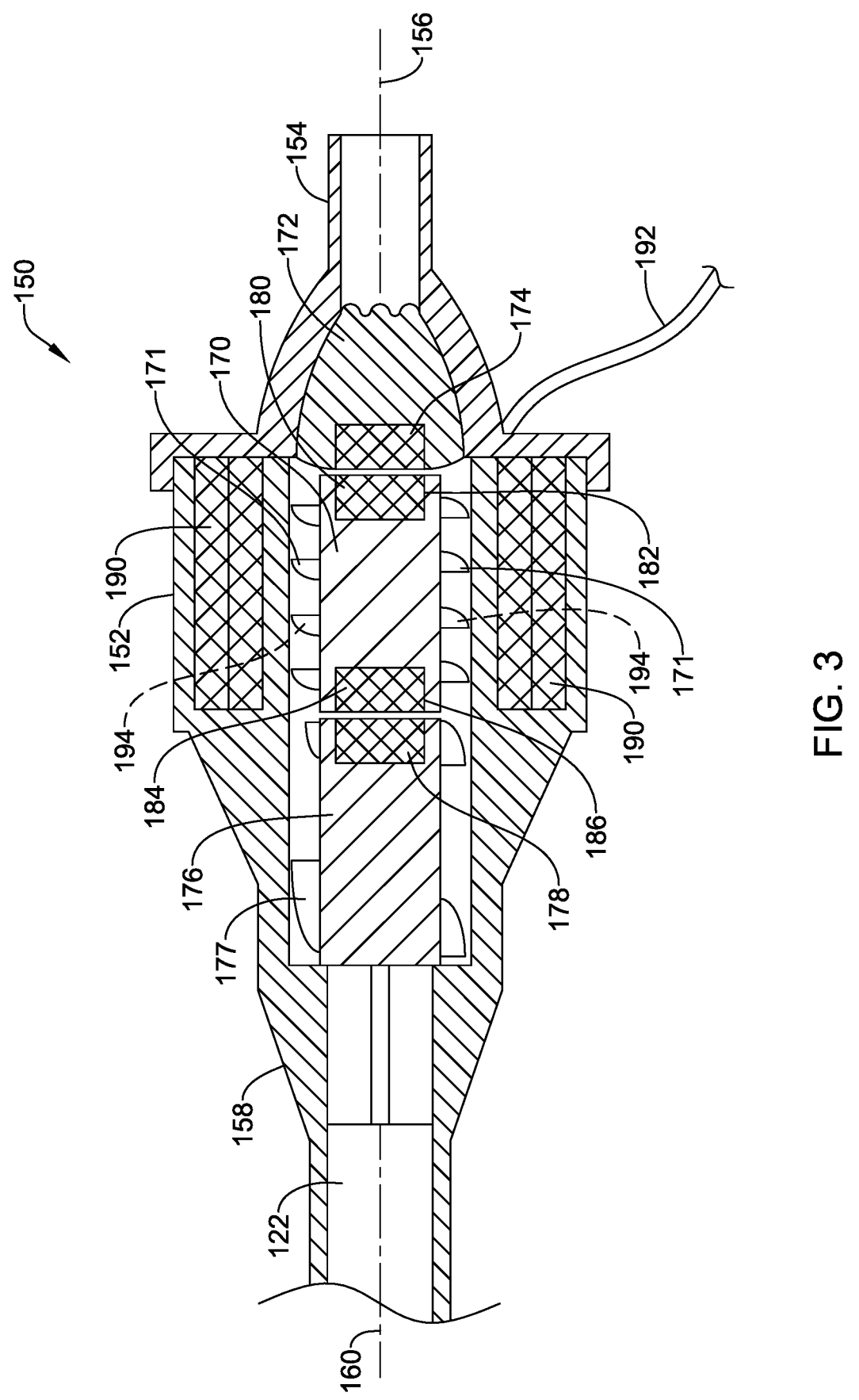
FIG. 3 illustrates selected aspects of the blood conditioning assembly of FIG. 2.
Figure 4:
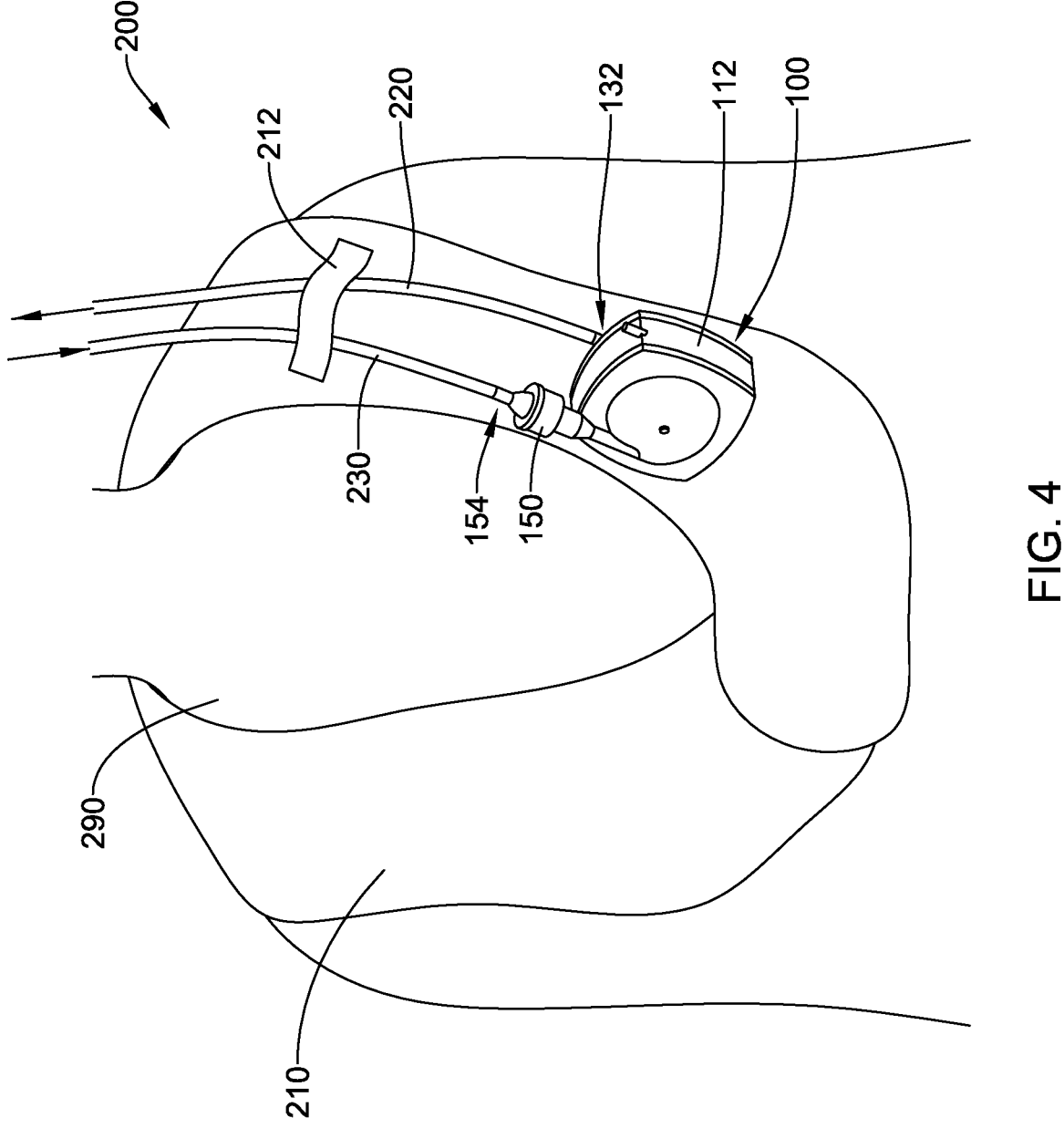
FIG. 4 illustrates selected aspects of an ECLS system utilizing the blood conditioning assembly of FIGS. 2-3.

FIGS. 2 and 3 illustrate selected aspects of a blood conditioning assembly 100 for use with an extracorporeal life support (ECLS) system (e.g., FIG. 4). In some embodiments, the blood conditioning assembly 100 may include an oxygenator 110. The oxygenator 110 may include a housing 112 and a gas exchanger 114 disposed within the housing 112. In some embodiments, the oxygenator 110 and/or the gas exchanger 114 may have similar construction and/or may function in a similar way to the device(s) disclosed in International Publication No. WO 2021/191661 A1, which is incorporated herein by reference in its entirety.

The oxygenator 110 and/or the housing 112 may include a venous cover 120 and an arterial cover 130 disposed on opposite sides of the gas exchanger 114. The oxygenator 110, the housing 112, and/or the venous cover 120 may include an inflow lumen 122 in fluid communication with the gas exchanger 114. In some embodiments, the housing 112 and/or the venous cover 120 may include a purging line port 124 through which air can be purged from the oxygenator 110 and/or the housing 112. In some embodiments, the purging line port 124 may be disposed proximate and/or at a center of the venous cover 120. The oxygenator 110, the housing 112, and/or the arterial cover 130 may include a blood outlet port 132 in fluid communication with the gas exchanger 114 and configured to connect to the extracorporeal life support system. The blood outlet port 132 may have and/or define a blood outlet flow axis 134. In at least some embodiments, the blood outlet port 132 may be disposed on an opposite side of the gas exchanger 114 from the inflow lumen 122.

The oxygenator 110 and/or the housing 112 may include a gas inlet port 140 in fluid communication with the gas exchanger 114. The gas inlet port 140 may be configured to connect to a gas supply source via polymeric tubing (not shown) to transport gas (e.g., oxygen, air, etc.) to the oxygenator 110. The oxygenator 110 and/or the housing 112 may include a gas outlet port 142 configured to transport gas (e.g., oxygen, air, etc.) away from the oxygenator 110. During use, gas may be transferred between the gas exchanger 114 and blood flowing through the oxygenator 110 (e.g., oxygen into the blood, carbon dioxide out of the blood, etc.).

The blood conditioning assembly 100 may include an axial pump 150 configured to drive fluid flow through the oxygenator 110. In some embodiments, the axial pump 150 may extend from the housing 112 and/or the venous cover 120 of the oxygenator 110. In some embodiments, the axial pump 150 may be fixedly attached directly to the oxygenator 110, the housing 112, and/or the venous cover 120. In some embodiments, the axial pump 150 may be integrally formed with the housing 112 and/or the venous cover 120 of the oxygenator 110. In at least some embodiments, the blood conditioning assembly 100 may be devoid of tubing between and/or connecting the axial pump 150 and the oxygenator 110. In some embodiments, the arrangement and/or positioning of the axial pump 150 and the oxygenator 110 in the blood conditioning assembly 100 may reduce and/or eliminate tubing and/or flow lines disposed exterior to the oxygenator 110 (e.g., the housing 112, the venous cover 120, etc.) and the axial pump 150. By reducing or eliminating such tubing, the volume of extracorporeal blood and/or fluid may be reduced, and drawbacks associated with the volume of extracorporeal blood and/or fluid may also be reduced or eliminated.

In some embodiments, the axial pump 150 may include a pump body 152. In some embodiments, the pump body 152 may be disposed tangentially on the venous cover 120 and/or the housing 112 of the oxygenator 110. In some embodiments, the pump body 152 may be integrally formed with the housing 112 and/or the venous cover 120 of the oxygenator 110. In some embodiments, the pump body 152 may be monolithically formed with the housing 112 and/or the venous cover 120 of the oxygenator as a single component, such as molded together during a molding process. In some embodiments, the axial pump 150 may be disposed coaxial with the inflow lumen 122 of the oxygenator 110, the housing 112, and/or the venous cover 120.

In some embodiments, the axial pump 150 and/or the pump body 152 may include an inlet 154 having and/or defining an inlet flow axis 156. The axial pump 150 and/or the pump body 152 may include an outlet 158 having and/or defining an outlet flow axis 160. In some embodiments, an inner surface of the outlet 158 may include grooves, channels, and/or an inward taper toward the inflow lumen 122. Other configurations are also contemplated. The inlet flow axis 156 may be parallel to the outlet flow axis 160. In some embodiments, the inlet flow axis 156 may be coaxial with the outlet flow axis 160. In at least some embodiments, the inlet flow axis 156 may be oriented generally parallel to the blood outlet flow axis 134. In some embodiments, the blood outlet port 132 is disposed on an opposite side of the gas exchanger 114 from the axial pump 150. As such, blood entering the housing 112 of the oxygenator 110 through the axial pump 150 and/or the inflow lumen 122 must pass through and/or around the gas exchanger 114 before exiting the housing 112 of the oxygenator 110 through the blood outlet port 132.

As seen in FIG. 3, the axial pump 150 may include a helical impeller 170 disposed within the pump body 152. In some embodiments, the helical impeller 170 may have and/or define a central axis that is oriented coaxial with the inlet flow axis 156. In some embodiments, the helical impeller 170 may have and/or define a central axis that is oriented coaxial with the outlet flow axis 160. In some embodiments, the helical impeller 170 may have and/or define a central axis that is oriented coaxial with the inlet flow axis 156 and the outlet flow axis 160. The helical impeller 170 may rotate about the central axis during operation of the axial pump 150 to propel blood through the oxygenator 110. The helical impeller 170 may include a generally cylindrical body portion and one or more helical blades 171 or fins extending radially outward from the generally cylindrical body portion. The one or more helical blades or fins may have and/or may be angled at a first pitch relative to the generally cylindrical body portion. The one or more helical blades 171 or fins may be configured to axially move blood or fluid from the inlet 154 toward the outlet 158 via rotation of the helical impeller 170. Rotation of the helical impeller 170 may be actuatable and/or controlled as discussed herein.

The axial pump 150 may include a diverter 172 disposed within the pump body 152 upstream of the helical impeller 170. In some embodiments, the diverter 172 may be disposed between the inlet 154 and the helical impeller 170. The diverter 172 may be configured to direct and/or divert blood and/or fluid entering the axial pump 150 via the inlet 154 toward the helical impeller 170. The diverter 172 may be shaped, sized, and configured to limit damage to blood cells. In some embodiments, the diverter 172 may include channels, grooves, ridges, guides, blades, etc. formed in or extending from a generally conical outer surface. The diverter 172 may be configured to direct blood flow radially outward from the central axis toward the helical blades 171 or fins of the helical impeller 170 as the blood flows through the axial pump 150. In some embodiments, the diverter 172 may be configured to straighten and/or smooth out blood or fluid flow entering the axial pump 150 and/or the pump body 152 from the inlet 154 to reduce hemolysis of red blood cells. In some embodiments, the diverter 172 may be fixedly secured to and/or within the pump body 152. In some embodiments, the diverter 172 may be nonrotatable relative to the pump body 152. Thus, the helical impeller 170 may rotate relative to the diverter 172. In some alternative embodiments, the diverter 172 may be movable and/or rotatable relative to the pump body 152.

The diverter 172 may include at least one upstream magnet 174 disposed within a recess formed in the diverter 172. In some embodiments, the diverter 172 may include at least one upstream magnet 174 fixedly attached to the diverter 172. In some embodiments, the diverter 172 may include at least one upstream magnet 174 at least partially embedded within the diverter 172. In some embodiments, the diverter 172 may include at least one upstream magnet 174 completely embedded within the diverter 172. Other configurations are also contemplated. The purpose of the at least one upstream magnet 174 is discussed in more detail below.

The axial pump 150 may include a rectifier 176 disposed within the pump body 152 downstream of the helical impeller 170. In some embodiments, the rectifier 176 may be disposed between the helical impeller 170 and the outlet 158. The rectifier 176 may be configured to direct blood and/or fluid exiting the helical impeller 170 axially toward the outlet 158. Blood and/or fluid traveling through the helical impeller 170 may take on or develop a circular or swirling flow around the helical impeller 170. The rectifier 176 may be configured to convert that circular or swirling flow of blood back to a more axial flow of blood directed toward the outlet 158. The rectifier 176 may be shaped, sized, and configured to limit damage to blood cells. In some embodiments, the rectifier 176 may include channels, grooves, ridges, guides, blades, etc. formed in or extending from a generally cylindrical body. In some embodiments, the rectifier 176 may include a helical ridge 177 extending along and/or radially outward from an outer surface of the generally cylindrical body. In some embodiments, the channels, grooves, ridges, guides, blades, the helical ridge 177, etc. formed in or extending from the generally cylindrical body may have and/or be angled at a second pitch relative to the generally cylindrical body that is different from the first pitch of the one or more helical blades 171 or fins of the helical impeller 170. In some instances the second pitch of the helical ridge 177 of the rectifier 176 may be greater than the first pitch of the helical blade(s) 171. The difference in pitch of these elements may help to convert circular flow to axial flow by urging and/or forcing the blood or fluid to move in a more axial direction. In some embodiments, the rectifier 176 may be stationary relative to the pump body 152. In some embodiments, the rectifier 176 may be fixedly secured to and/or within the pump body 152. In some embodiments, the rectifier 176 may be nonrotatable relative to the pump body 152. Thus, the helical impeller 170 may rotate relative to the rectifier 176. In some alternative embodiments, the rectifier 176 may be movable and/or rotatable relative to the pump body 152. For example, in some instances the rectifier 176, which may be rotatably suspended in the pump body 152, may freely rotate relative to the pump body 152 as blood flows across the rectifier 176.

The rectifier 176 may include at least one downstream magnet 178 disposed within a recess formed in the rectifier 176. In some embodiments, the rectifier 176 may include at least one downstream magnet 178 fixedly attached to the rectifier 176. In some embodiments, the rectifier 176 may include at least one downstream magnet 178 at least partially embedded within the rectifier 176. In some embodiments, the rectifier 176 may include at least one downstream magnet 178 completely embedded within the rectifier 176. Other configurations are also contemplated. The purpose of the at least one downstream magnet 178 is discussed in more detail below.

The helical impeller 170 may be rotatable within and/or relative to the pump body 152 of the axial pump 150. In some embodiments, the helical impeller 170 may be magnetically suspended within the pump body 152 of the axial pump 150. In some embodiments, the helical impeller 170 may be magnetically suspended along its central longitudinal axis and/or may be oriented coaxial with the inlet flow axis 156 and/or the outlet flow axis 160.

In some embodiments, the helical impeller 170 may include at least one first magnet 180 disposed within a first recess 182 formed in the helical impeller 170 at and/or proximate an upstream end of the helical impeller 170. In some embodiments, the helical impeller 170 may include at least one first magnet 180 fixedly attached to the helical impeller 170 at and/or proximate the upstream end of the helical impeller 170. In some embodiments, the helical impeller 170 may include at least one first magnet 180 at least partially embedded in the helical impeller 170 at and/or proximate the upstream end of the helical impeller 170. In some embodiments, the helical impeller 170 may include at least one first magnet 180 completely embedded in the helical impeller 170 at and/or proximate the upstream end of the helical impeller 170. Other configurations are also contemplated.

In some embodiments, the helical impeller 170 may include at least one second magnet 184 disposed within a second recess 186 formed in the helical impeller 170 at and/or proximate a downstream end of the helical impeller 170. In some embodiments, the helical impeller 170 may include at least one second magnet 184 fixedly attached to the helical impeller 170 at and/or proximate the downstream end of the helical impeller 170. In some embodiments, the helical impeller 170 may include at least one second magnet 184 at least partially embedded in the helical impeller 170 at and/or proximate the downstream end of the helical impeller 170. In some embodiments, the helical impeller 170 may include at least one second magnet 184 completely embedded in the helical impeller 170 at and/or proximate the downstream end of the helical impeller 170. Other configurations are also contemplated.

In at least some embodiments, the at least one second magnet 184 may be aligned with and/or may be coaxial with the at least one first magnet 180 and/or the central longitudinal axis of the helical impeller. The at least one first magnet 180 may be aligned with and/or may be coaxial with the at least one upstream magnet 174 and/or the inlet flow axis 156. The at least one second magnet 184 may be aligned with and/or may be coaxial with the at least one downstream magnet 178 and/or the outlet flow axis 160. Accordingly, the helical impeller 170 may be magnetically suspended within the pump body 152 along the central longitudinal axis of the helical impeller 170 and/or the pump body 152 between the diverter 172 and/or the at least one upstream magnet 174 and the rectifier 176 and/or the at least one downstream magnet 178.

Magnetic suspension of the helical impeller 170 within the pump body 152 may permit the helical impeller 170 to rotate relative to the pump body 152 without any physical bearing(s) and/or source of friction that may cause heat generation and/or damage to blood cells. In some embodiments, one or more magnets (e.g., the at least one upstream magnet 174, the at least one downstream magnet 178, the at least one first magnet 180, and/or the at least one second magnet 184) may prevent physical contact between the helical impeller 170 and the pump body 152. In at least some embodiments, the at least one upstream magnet 174, the at least one downstream magnet 178, the at least one first magnet 180, and/or the at least one second magnet 184 may be permanent high-performance magnets. Other configurations are also contemplated.

In some embodiments, the axial pump 150 may include one or more stator windings 190. In some embodiments, the one or more stator windings 190 may be disposed within the pump body 152. The one or more stator windings 190 may be radially spaced apart from the helical impeller 170. In some embodiments, the one or more stator windings 190 and/or the axial pump 150 may be electrically coupled to an electronic controller (not shown) via an electrical connection 192. In some embodiments, the electronic controller may be in wireless communication with the axial pump 150. In some alternative embodiments, the electronic controller may be integrated into the axial pump 150. Other configurations are also contemplated. The helical impeller 170 may include a plurality of magnets 194 disposed within and/or embedded within the one or more helical blades 171 or fins of the helical impeller 170. Other configurations and/or locations for the plurality of magnets 194 are also contemplated. The plurality of magnets 194 may be configured to interact with and/or respond to a rotating magnetic field generated by the one or more stator windings 190 to cause rotation of the helical impeller 170. In some embodiments, the plurality of magnets 194 may be permanent high-performance magnets. In at least some embodiments, the plurality of magnets 194 may be rare earth magnets.

FIG. 4 illustrates aspects of an extracorporeal life support system 200 incorporating the blood conditioning assembly 100 of the current disclosure, as described herein. In some embodiments, the extracorporeal life support system 200 may include a wearable support garment 210 (e.g., a strap or belt, a vest such as the VoyagerVest® from CardiacAssist, Inc., etc.), thereby rendering the extracorporeal life support system 200 more portable than previous systems utilizing a trolley. The blood conditioning assembly 100 (e.g., the oxygenator 110 and the axial pump 150, etc.) may be secured to the wearable support garment 210. In some embodiments, the blood conditioning assembly 100 (e.g., the oxygenator 110 and the axial pump 150, etc.) may be releasably secured to the wearable support garment 210 to facilitate replacement and/or cleaning of the blood conditioning assembly 100 and/or reuse of the wearable support garment 210 (with appropriate cleaning and/or disinfection). In one example, the blood conditioning assembly 100 (e.g., the oxygenator 110 and the axial pump 150, etc.) may be releasably secured to the wearable support garment 210 using straps, hook and loop closures, snaps, pins, buttons, etc. Other configurations are also contemplated.

The extracorporeal life support system 200 may include an arterial flow tube 220 fluidly connectable to an artery of a patient 290 and coupled to the blood outlet port 132 of the housing 112. In use, the extracorporeal life support system 200 may include an arterial flow tube 220 fluidly connected to an artery of a patient 290 and coupled to the blood outlet port 132 of the housing 112. The extracorporeal life support system 200 may include a venous flow tube 230 fluidly connectable to a vein of the patient 290 and coupled to the inlet 154 of the axial pump 150. In use, the extracorporeal life support system 200 may include a venous flow tube 230 fluidly connected to a vein of the patient 290 and coupled to the inlet 154 of the axial pump 150. In some embodiments, the arterial flow tube 220 and/or the venous flow tube 230 may be releasably secured to the wearable support garment 210 using one or more straps 212, clips, hook and loop closures, or other securement mechanisms. In some embodiments, the arterial flow tube 220 and/or the venous flow tube 230 may be movable relative to the wearable support garment 210 to facilitate movement and/or ambulation of the patient 290. Other configurations are also contemplated.

The blood conditioning assembly 100 and/or the arrangement thereof (e.g., having the axial pump 150 integrated into the housing 112 of the oxygenator 110) eliminates the blood transfer line 44 found in the extracorporeal life support system 10 of FIG. 1, thereby reducing the volume of extracorporeal blood or fluid as well as the drawbacks associated therewith. For example, the total volume of extracorporcal blood in the blood conditioning assembly 100 from the inlet 154 of the axial pump 154, through the oxygenator 110, to the outlet blood outlet port 132, may be 200 ml or less, may be 150 ml or less, may be 100 ml or less, or another suitable range. In some embodiments, a priming volume of the blood conditioning assembly 100 may depend on patient size. For example, some ECLS devices may be designed for adult patients or pediatric patients. Other configurations are also contemplated. Additionally, use of the axial pump 150 may reduce or eliminate drawbacks and/or complications associated with the use of a centrifugal pump (e.g., blood cell hemolysis, etc.).

In at least some embodiments, the extracorporeal life support system 200 may be configured to run on or be powered by batteries or another portable power source, thereby further enhancing the portability of the extracorporeal life support system 200 and/or providing a back-up in case of main electrical failure. For example, a battery or other portable power source may be provided with the wearable support garment 210.

In some embodiments, the extracorporeal life support system 200 may include one or more integrated blood sensors. For example, the one or more integrated blood sensors may be configured to monitor and/or measure pressure, oxygen saturation, temperature, the presence of air bubbles, etc. Other sensors and/or configurations are also contemplated. In some embodiments, the one or more integrated blood sensors may improve control and/or reduce complexity of the extracorporeal life support system 200.

The materials that can be used for the various components of the blood conditioning assembly and the various elements thereof disclosed herein may include those commonly associated with medical devices. For simplicity purposes, the following discussion refers to the device. However, this is not intended to limit the devices, components, and methods described herein, as the discussion may be applied to other elements, members, components, or devices disclosed herein, such as, but not limited to, the housing, the arterial cover, the venous cover, the tubing, the pump body, the helical impeller, the diverter, the rectifier, etc. and/or elements or components thereof.

In some embodiments, the device and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM), polyether block ester, polyurethane, polypropylene (PP), polyvinylchloride (PVC), polyether-ester, ether or ester based copolymers (for example, butylene/poly (alkylene ether) phthalate and/or other polyester elastomers), polyamide, elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, linear low density polyethylene, polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide, polysulfone, nylon, nylon-12, perfluoro (propyl vinyl ether) (PFA), ethylene vinyl alcohol, polyolefin, polystyrene, epoxy, polyvinylidene chloride (PVdC), poly(styrene-b-isobutylene-b-styrene), polycarbonates, polyisobutylene (PIB), polyisobutylene polyurethane (PIBU), polyurethane silicone copolymers, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V. 304L, and 316LV stainless steel; mild steel; nickel-titanium alloy such as linear elastic and/or super-elastic nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; titanium; combinations thereof; or any other suitable material.

In some embodiments, the device and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-protein and/or anti-bacterial agents (such as 2-methacryroyloxyethyl phosphorylcholine (MPC) and its polymers or copolymers); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed:

1. A blood conditioning assembly for use with an extracorporeal life support system, comprising:
  an oxygenator including a housing and a gas exchanger disposed within the housing; and
  an axial pump extending from the housing and configured to drive fluid flow through the oxygenator;
  wherein the axial pump is integrally formed with the housing of the oxygenator;
  wherein the axial pump includes a helical impeller having one or more magnets embedded therein that interact with a rotating magnetic field generated by one or more stator windings disposed within an axially extending cavity formed in a cylindrical portion of a pump body of the axial pump, the axially extending cavity being open at an upstream end of the cylindrical portion of the pump body;
  wherein the helical impeller is magnetically suspended within the pump body to prevent physical contact between the helical impeller and the pump body;
  wherein the pump body includes an inlet cover secured to an upstream end of the cylindrical portion of pump body;
  wherein the inlet cover includes a radially extending wall enclosing the axially extending cavity formed in the cylindrical portion of the pump body such that the one or more stator windings are entirely contained within the cavity formed in the cylindrical portion of the pump body.

2. The blood conditioning assembly of claim 1, wherein the housing includes a blood outlet port configured to connect to the extracorporeal life support system.

3. The blood conditioning assembly of claim 2, wherein the blood outlet port is disposed on an opposite side of the gas exchanger from the axial pump.

4. The blood conditioning assembly of claim 1, wherein the axial pump includes an inlet having an inlet flow axis and an outlet having an outlet flow axis, wherein the inlet flow axis is coaxial with the outlet flow axis.

5. The blood conditioning assembly of claim 1, wherein the axial pump includes a rectifier disposed downstream of the helical impeller.

6. The blood conditioning assembly of claim 5, wherein the rectifier is stationary with respect to the pump body.

7. The blood conditioning assembly of claim 5, wherein the rectifier includes a cylindrical body and a helical ridge extending along an outer surface of the cylindrical body.

8. A blood conditioning assembly for use with an extracorporeal life support system, comprising:
  an oxygenator including a housing and a gas exchanger disposed within the housing; and
  an axial pump configured to drive fluid flow through the oxygenator;
  wherein the blood conditioning assembly is devoid of external tubing between the axial pump and the oxygenator;
  wherein the axial pump includes a helical impeller having one or more magnets embedded therein that interact with a rotating magnetic field generated by one or more stator windings disposed within a cylindrical portion of the pump body;
  wherein the helical impeller is magnetically suspended within the pump body to prevent physical contact between the helical impeller and the pump body;
  wherein the pump body includes an inlet cover secured to an upstream end of the cylindrical portion of the pump body, the inlet cover including a wall enclosing the one or more stator windings within a cavity formed in the cylindrical portion of the pump body;
  wherein a downstream end of the inlet surrounds the upstream end of the cylindrical portion of the pump body.

9. The blood conditioning assembly of claim 8, wherein the axial pump is disposed coaxial with an inflow lumen of the oxygenator.

10. The blood conditioning assembly of claim 8, wherein the axial pump includes an inlet having an inlet flow axis and the housing includes a blood outlet port having a blood outlet flow axis, wherein the inlet flow axis is generally parallel to the blood outlet flow axis.

11. An extracorporeal life support system, comprising:
  a blood conditioning assembly including:
    an oxygenator including a housing and a gas exchanger disposed within the housing; and
    an axial pump configured to drive fluid flow through the oxygenator;
    wherein the axial pump is fixedly attached directly to the oxygenator; and
    wherein the axial pump includes a pump body integrally formed with the housing;
    wherein the axial pump includes a helical impeller having one or more magnets embedded therein that interact with a rotating magnetic field generated by one or more stator windings disposed within a cylindrical portion of the pump body;

wherein the helical impeller is magnetically suspended within the pump body to prevent physical contact between the helical impeller and the pump body;

wherein the pump body includes an inlet cover secured to an upstream end of the cylindrical portion of the pump body, the inlet cover including a wall enclosing the one or more stator windings within a cavity formed in the cylindrical portion of the pump body;

wherein a downstream end of the inlet cover surrounds the upstream end of the cylindrical portion of the pump body;

an arterial flow tube fluidly connected to an artery of a patient and coupled to a blood outlet port of the housing; and a venous flow tube fluidly connected to a vein of the patient and coupled to an inlet of the axial pump.

12. The extracorporeal life support system of claim 11, wherein the housing includes a venous cover and an arterial cover disposed on opposite sides of the gas exchanger.

13. The extracorporeal life support system of claim 12, wherein the pump body is disposed tangentially on the venous cover.

14. The extracorporeal life support system of claim 11, wherein the helical impeller is rotatable relative to the pump body.

* * * * *